United States Patent
Rainbird

(10) Patent No.: US 8,835,356 B2
(45) Date of Patent: Sep. 16, 2014

(54) HIGH LOAD GLYPHOSATE FORMULATIONS

(75) Inventor: Ross Rainbird, Applecross (AU)

(73) Assignee: Imtrade Australia Pty Ltd, Como (AU)

( * ) Notice: Subject to any disclaimer, the term of this patent is extended or adjusted under 35 U.S.C. 154(b) by 0 days.

(21) Appl. No.: 13/509,242

(22) PCT Filed: Nov. 16, 2010

(86) PCT No.: PCT/AU2010/001535
§ 371 (c)(1),
(2), (4) Date: May 10, 2012

(87) PCT Pub. No.: WO2011/057361
PCT Pub. Date: May 19, 2011

(65) Prior Publication Data
US 2012/0231956 A1    Sep. 13, 2012

(30) Foreign Application Priority Data
Nov. 16, 2009  (AU) ................................. 2009905595

(51) Int. Cl.
*A01N 57/18*  (2006.01)
*A01N 57/20*  (2006.01)
(52) U.S. Cl.
CPC ..................................... *A01N 57/20* (2013.01)
USPC ....................................................... 504/206
(58) Field of Classification Search
None
See application file for complete search history.

(56) References Cited

U.S. PATENT DOCUMENTS

| | | |
|---|---|---|
| 3,799,758 A | 3/1974 | Franz |
| 3,853,530 A | 12/1974 | Franz |
| 3,977,860 A | 8/1976 | Franz |
| 4,140,513 A | 2/1979 | Prill |
| 4,315,765 A | 2/1982 | Large |
| 4,405,531 A | 9/1983 | Franz |
| 4,481,026 A | 11/1984 | Prisbylla |
| 4,507,251 A | 3/1985 | Soriano et al. |
| 5,998,332 A | 12/1999 | Sato et al. |
| 6,277,788 B1 | 8/2001 | Wright |
| 6,544,930 B2 | 4/2003 | Wright |
| 6,747,164 B2 | 6/2004 | Gustavsson et al. |
| 6,881,707 B2 | 4/2005 | Howat et al. |
| 7,049,270 B2 | 5/2006 | Lennon et al. |
| 2006/0270556 A1 * | 11/2006 | Wright et al. ................. 504/165 |

FOREIGN PATENT DOCUMENTS

| | | | |
|---|---|---|---|
| WO | WO02/069718 | | 9/2002 |
| WO | WO-02069718 | * | 9/2002 |
| WO | WO03/013241 | | 2/2003 |
| WO | WO2006/023431 | | 3/2006 |
| WO | WO-2006023431 | * | 3/2006 |
| WO | WO2007/109791 | | 9/2007 |
| WO | WO-2007109791 | * | 9/2007 |

* cited by examiner

*Primary Examiner* — Alton Pryor
(74) *Attorney, Agent, or Firm* — Moss & Barnett

(57) ABSTRACT

A liquid formulation containing at least about 500 ae g/L, and up to 625 ae g/L or more, of glyphosate, a surfactant that is efficacy-enhancing for glyphosate and is compatible with potassium glyphosate and which constitutes less than about 100 g/L of the formulation, non-amphiphilic cations, the majority of which are potassium cations, a low molecular weight acid or conjugate base thereof that is chemically distinct from glyphosate, and water.

24 Claims, No Drawings

HIGH LOAD GLYPHOSATE FORMULATIONS

FIELD OF THE INVENTION

This invention relates to liquid formulations of glyphosate that include glyphosate at a level of at least 500 grams per liter on an acid equivalent (ae) basis. In particular this invention relates to high-load liquid formulations of glyphosate that includes a surfactant of a type and at sufficiently high level that enhances the efficacy of glyphosate and permits the formulation to be used without the further addition of surface active agents. Here and henceforth, such surfactants will be denoted as surfactants that are efficacy-enhancing for glyphosate. The use of the formulations of this invention may involve adding them to water prior to application by spraying.

BACKGROUND TO THE INVENTION

Liquid glyphosate formulations that include efficacy-enhancing surfactants are widely used to control weeds. Such formulations have been described in U.S. Pat. Nos. 4,507,250, 4,481,026, 4,405,531, 4,315,765, 4,140,513, 3,977,860, 3,853,530 and 3,799,758. Such formulations generally comprise a glyphosate salt, for example the isopropylammonium salt, and an efficacy-enhancing surfactant, for example tallowamine ethoxylate.

The recent development of solution concentrates of glyphosate has involved the identification of salts and surfactants that enable higher levels of glyphosate ae to be provided in a given volume without loss of efficacy relative to well-established glyphosate formulations (eg Roundup made by Monsanto).

The achievement of higher loading glyphosate formulations is important because:

in a highly competitive market, farmers will pay a premium for the product which contains the highest loading of glyphosate, and a given quantity of glyphosate ae can be transported and stored in a more compact container if the loading of glyphosate ae in the formulation (on a volume basis) is higher—this has been extensively discussed in U.S. Pat. No. 6,544,930 (Wright, filed 2001, assigned to Monsanto).

The following methods for increasing the loading of glyphosate ae in a formulation have been proposed.

In U.S. Pat. No. 5,998,332 (Sato et al, filed 1998, assigned to Monsanto) there is described an aqueous herbicidal composition comprising an ammonium salt of glyphosate in an amount between 10-50% ae by weight. It is stated that there is a difficulty in defining suitable surfactants for use with sodium glyphosate in a liquid formulation. Example 1 in this application provides a method of formulating liquid glyphosate at 470 ae g/L in a formulation that includes surfactant. Example 4 provides a method for formulating liquid glyphosate at 540 ae g/L in the presence of surfactant.

In U.S. Pat. No. 6,277,788 (Wright, filed 1999, assigned to Monsanto) there is described a herbicidal composition comprising glyphosate predominantly in the form of the monoethanolammonium salt in an amount of about 360 to 570 ae g/L. In the discussion associated with Table 7 in this application, it is stated that at the extremely high glyphosate concentrations of 540 ae g/L, there is scope for including sufficient surfactant to provide commercially acceptable herbicidal efficacy. Appropriate surfactants for use in these formulations include polyoxyethylene (5) cocoamines.

In U.S. Pat. No. 6,544,930 (Wright, filed 2001, assigned to Monsanto) there is described a storage and shipping system comprising a container substantially filled with an aqueous solution of glyphosate, predominantly in the form of one or a mixture of potassium and monoethanolammonium (MEA) salts thereof, the solution having a glyphosate ae concentration of at least 30%. In the text associated with Table 6 in this application, it is stated that a composition that contains glyphosate ae at a loading as high as 540 ae g/L is a significant advance in the art that could not have been predicted from prior knowledge of the surfactant or of glyphosate MEA salt.

In U.S. Pat. No. 7,049,270 (Lennon et al, filed 2001, assigned to Monsanto) there is described a formulation useful in retarding the growth of vegetation comprising an aqueous mixture containing a surfactant, glyphosate primarily as potassium salt, and a dicarboxylic acid. In the examples of this specification, the highest loading of glyphosate in a formulation also comprising surfactant appears to be 542 ae g/L.

In WO 2006/023431, corresponding to PCT/US2005/028930 (Eaton et al, assigned to Monsanto) it is stated that there is an especial need for formulations having high glyphosate loadings. This application teaches: a mixed salt aqueous glyphosate formulation where the glyphosate concentration is not less than 360 ae g/L, wherein (a) the glyphosate is in anionic form accompanied by low molecular weight non-amphiphilic cations in a total molar amount of about 100% to 120% of the molar amount of glyphosate; (b) said cations comprise potassium and propylammonium cations in a mole ratio of 70:30 to 90:10 and (c) said potassium and propylammonium cations together consisting of all low molecular weight non-amphiphilic cations in the composition. In table 2 which is associated with example 2 in the application, two formulations are described in which target concentrations of glyphosate are said to be 600 ae g/L. A footnote to the table explains that in fact the achieved concentration of glyphosate in these formulations was 590 ae g/L, due to raw material concentration limits.

The above literature shows that in spite of significant effort by a well-resourced multi-national company, the maximum level of glyphosate that can be incorporated in an aqueous formulation comprising efficacy-enhancing surfactant is 590 ae g/L.

U.S. Pat. No. 6,747,164 (Gustasson and Weuste, filed 2001, assigned to Akzo Nobel) describes amine compounds with improved biodegradability as adjuvants for pesticides and fertilisers. The amino compound is an esteramine or amidoamine surfactant. The enteramines are obtained from an ethoxylated alcohol that has been carboxymethylated and then esterified with a tertiary hydroxyamine (alkanolamine), and the amidoamines are obtained by a reaction between a fatty acid or a fatty acid methyl ester and a diamine, such as N,N-bishydroxyethyl-1,3 propylenediamine. Claim 12 in this specification notes the use of these adjuvants with glyphosate or glyphosate salts. There is no reference in this patent to high-loading formulations of glyphosate.

U.S. Pat. No. 6,881,707 (Howat and Hay, assigned to Nufarm) describes a glyphosate composition comprising a mixture of salts of glyphosate comprising each of potassium and isopropylammonium salts. None of the formulations in this application has a loading of glyphosate in excess of 500 ae g/L, and there is no suggestion in this specification that high glyphosate loadings can be achieved using the teachings provided. Furthermore the specification asserts that the use of specific combinations of low molecular weight non-amphiphilic cations leads to a significant improvement in the bioefficacy of the glyphosate composition.

There is an ongoing need to provide higher-loading liquid glyphosate formulations which comprise efficacy-enhancing surfactants.

DESCRIPTION OF THE INVENTION

According to one aspect of the present invention there is provided a liquid formulation containing at least about 500 ae g/L of glyphosate, a surfactant that is efficacy-enhancing for glyphosate and is compatible with potassium glyphosate and which constitutes less than about 100 g/L of the formulation, non-amphiphilic cations, the majority of which are potassium cations, at least one low molecular weight acid or conjugate base of a low molecular weight acid that is chemically distinct from glyphosate, and water.

Preferably, a liquid formulation of the present invention contains at least 570 ae g/L of glyphosate, more preferably at least 600 ae g/L glyphosate, and even more preferably at least 620 ae g/L glyphosate.

The liquid formulations may additionally contain glyphosate-associated impurities, which are typically about 5% of the glyphosate ae content.

Preferably, the liquid formulation of the present invention contains both potassium and iso-propylammonium non-amphilic cations having respectively a mole ratio in the range 99:1 to 65:35. More preferably, the mole ratio is in the range 96:4 to 80:20.

In one preference, the surfactant that is efficacy-enhancing for glyphosate is present at less than about 70 g/L in the formulation.

Surfactants that are compatible with potassium glyphosate in concentrated formulation have been discussed in U.S. Pat. No. 7,049,270, the contents of which are incorporated by reference. This patent discusses monoalkoxylated amine surfactants, alkoxylated poly(hydroxyalkyl)amine surfactants, di-poly(hydroxyalkyl)amine surfactants, alkoxylated triamine surfactants, amine oxide surfactants, alkoxylated amine oxide surfactants, alkoxylated diamine surfactants, dialkoxylated amine surfactants, dialkoxylated alcohol surfactants.

Esteramine and amido amine surfactants and surfactant blends that are efficacy-enhancing for glyphosate have been discussed in depth in U.S. Pat. No. 6,747,164, the contents of which are incorporated by reference. Specific examples (among many) of these surfactants and surfactant blends include: cocoamide of N,N-bishydroxyethyl-1,3-propylenediamine, and a blend of 80% cocoamide of N,N-bishydroxyethyl-1,3-propylenediamine and 20% hexyl glucoside. Coco amidopropyldimethylamine, which is the cocoamide of N,N-bismethyl-1,3-propylenediamine, has been promoted as compatible with potassium glyphosate and as efficacy enhancing for glyphosate (as IPA salt) at levels as low as 6% on total formulation.

In one preference, the surfactant that is efficacy-enhancing for glyphosate comprises an amino group with basic character.

Preferably, the surfactant that is efficacy-enhancing for glyphosate is selected from the group that includes amido-amine surfactants and ester-amine surfactants. More preferably the surfactant that is efficacy-enhancing for glyphosate is selected from the group of amido-amine surfactants.

In one preference, the surfactant that is efficacy-enhancing for glyphosate can be represented by R1-amidopropylamino-R2,R3, where R1 is preferably chosen from branched or straight C8-C18 alkyl radicals, and R2, R3 are independently chosen from branched or straight C1-C4 alkyl radicals. In another preference the surfactant that is efficacy-enhancing for glyphosate can be represented by R1-amidoalkylamino-R2,R3 where R1 is selected from the group comprising branched or straight C8-C18 alkyl radicals and R2,R3 are independently chosen from branched or straight C2-C8 alkyl radicals. Even more preferably, the surfactant that is efficacy-enhancing for glyphosate comprises coco amidopropyl dimethylamine moieties. These are the amide reaction products of coco fatty acid and N1,N1-dimethyl-1,3-diaminopropane.

In one preference, the liquid formulation of the invention comprises at least about 400 g/L of water, more preferably at least about 420 g/L of water. However, in another preference the liquid formulation of the invention contains less than about 400 g/L of water. In one especially preferred liquid formulation of the invention the water content is about 377 g/L. Provided that high levels of glyphosate are achieved, it is advantageous that high levels of water are provided in the formulation since water is inexpensive and also environmentally beneficial.

In one preference, the acid that is chemically distinct from glyphosate has a molecular weight of less than about 1000, preferably less than about 300, more preferably less than about 200. The low molecular weight acid or conjugate base thereof is derived from moieties in the set consisting of acetic acid, boric acid, citric acid, formic acid, hydrochlorid acid, phosphoric acid, phosphorous acid, propionic acid, hypophosphorous acid, sodium tripolyphosphate or another salt of tripolyphospate, tetrasodium pyrophosphate or another salt of pyrophosphate. In one preference, the acid is phosphoric acid.

In one preference, the surfactant that is efficacy-enhancing for glyphosate is conditioned prior to use in the formulation. The conditioning step may involve the addition of a low molecular weight acid or conjugate base thereof to the surfactant. In one preference, the conditioning step involves the addition of water as well as the addition of a low molecular weight acid or conjugate base thereof to the surfactant. The result of the conditioning step is called the "wetter package" throughout this specification. It is preferred to form the wetter package as once it has been formed there is no need to handle high strength acid or conjugate base thereof in manufacturing and, additionally, the wetter package liquid is less viscous than the unconditioned surfactant.

In one preference, the conditioning step involves taking one part by weight of surfactant that is efficacy-enhancing for glyphosate and mixing together 0.2-3 parts water and 0.01-0.5 parts phosphoric acid.

Preferably liquid formulations according to the present invention have viscosities of 1000 cP or less, measured on a Brookfield viscometer at 20° C. More preferably the viscosities of the formulations are 500 cP or less, and even more preferably the said viscosities are 250 cP or less.

DESCRIPTION OF EMBODIMENTS OF THE INVENTION

In order that the present invention may be more clearly understood reference is made to the following examples, some of which are preferred embodiments of the present invention.

EXAMPLE E1

Glyphosate technical (95% purity), potassium hydroxide (45% in water), mono-isopropylamine, wetter package and water were combined in the ratio 632 parts, 447 parts, 49 parts, 160 parts, and 95 parts by weight respectively to provide 1383 parts of a formulation having a density of 1.383. The wetter package was made by combining 37.5 parts S118, 9.7 parts 85% phosphoric acid and 52.8 parts by weight of water. S118 is an amidoamine surfactant predominantly comprising cocoamidopropyl dimethylamine being the amide reaction product of coco fatty acid and N1,N1-dimethyl-1,3-diaminopropane. The weight composition of one liter of the final formulation was

| Component | Grams weight in 1 litre |
| --- | --- |
| glyphosate | 600.4 |
| glyphosate-derived impurity | 31.6 |
| potassium hydroxide | 201.15 |
| S118 | 60 |
| phosphoric acid | 13.19 |
| phosphoric acid-derived impurity | 2.33 |
| monoisopropylamine | 49 |
| water | 425.33 |

EXAMPLE E2

Glyphosate technical (95% purity), potassium hydroxide (45% in water), mono-isopropylamine, wetter package and water were combined in the ratio 632 parts, 532 parts, 11 parts, 160 parts, and 45 parts by weight respectively to provide 1380 parts of a formulation having a density of 1.380. The wetter package was made by combining 37.5 parts S118, 9.7 parts 85% phosphoric acid and 52.8 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 239.2 |
| S118 | 60 |
| phosphoric acid | 13.19 |
| phosphoric acid-derived impurity | 2.33 |
| monoisopropylamine | 10.95 |
| water | 423 |

EXAMPLE E3

Glyphosate technical (95% purity), potassium hydroxide (45% in water), mono-isopropylamine, wetter package and water were combined in the ratio 632 parts, 532 parts, 11 parts, 160 parts, and 45 parts by weight respectively to provide 1380 parts of a formulation having a density of 1.380. The wetter package was made by combining 37.5 parts S118, 4.9 parts 85% phosphoric acid and 57.6 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 239.2 |
| S118 | 60 |
| phosphoric acid | 6.66 |
| phosphoric acid-derived impurity | 1.18 |
| monoisopropylamine | 10.95 |
| water | 430 |

EXAMPLE E4

Glyphosate technical (95% purity), potassium hydroxide (45% in water), mono-isopropylamine, wetter package and water were combined in the ratio 632 parts, 532 parts, 11 parts, 160 parts, and 45 parts by weight respectively to provide 1380 parts of a formulation having a density of 1.380. The wetter package was made by combining 37.5 parts S118; 2.5 parts 85% phosphoric acid and 60 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 239.2 |
| S118 | 60 |
| phosphoric acid | 3.4 |
| phosphoric acid-derived impurity | 0.6 |
| monoisopropylamine | 10.95 |
| water | 434 |

EXAMPLE E5

Glyphosate technical (95% purity), potassium hydroxide (45% in water), mono-isopropylamine, wetter package and water were combined in the ratio 632 parts, 448 parts, 44 parts, 160 parts, and 96 parts by weight respectively to provide 1380 parts of a formulation having a density of 1.380. The wetter package was made by combining 37.5 parts S118, 4.9 parts 85% phosphoric acid and 57.6 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 201.4 |
| S118 | 60 |
| phosphoric acid | 6.66 |
| phosphoric acid-derived impurity | 1.18 |
| monoisopropylamine | 43.81 |
| water | 435 |

EXAMPLE E6

Glyphosate technical (95% purity), potassium hydroxide (45% in water), mono-isopropylamine, wetter package and water were combined in the ratio 632 parts, 448 parts, 44 parts, 160 parts, and 94 parts by weight respectively to provide 1378 parts of a formulation having a density of 1.378. The wetter package was made by combining 37.5 parts S118, 2.5 parts 85% phosphoric acid and 60 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 201.4 |
| S118 | 60 |
| phosphoric acid | 3.4 |
| phosphoric acid-derived impurity | 0.6 |
| monoisopropylamine | 43.81 |
| water | 437 |

EXAMPLE E7

Glyphosate technical (95% purity), potassium hydroxide (45% in water), mono-isopropylamine, wetter package and water were combined in the ratio 632 parts, 532 parts, 11 parts, 160 parts, and 44 parts by weight respectively to provide 1379 parts of a formulation having a density of 1.379. The wetter package was undiluted S118. The weight composition of one liter of the final formulation was

| Component | Grams weight in 1 litre |
| --- | --- |
| glyphosate | 600.3 |
| glyphosate-derived impurity | 31.3 |
| potassium hydroxide | 239.2 |
| S118 | 160 |
| phosphoric acid | 0 |
| phosphoric acid-derived impurity | 0 |
| monoisopropylamine | 10.95 |
| water | 337 |

EXAMPLE E8

Glyphosate technical (95% purity), potassium hydroxide (45% in water), mono-isopropylamine, wetter package and water were combined in the ratio 632 parts, 336 parts, 88 parts, 160 parts, and 162 parts by weight respectively to provide 1378 parts of a formulation having a density of 1.378. The wetter package was made by combining 37.5 parts S118, 9.7 parts 85% phosphoric acid and 52.8 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 151.1 |
| S118 | 60 |
| phosphoric acid | 13.19 |
| phosphoric acid-derived impurity | 2.33 |
| monoisopropylamine | 87.62 |
| water | 432 |

EXAMPLE E9

Glyphosate technical (95% purity), potassium hydroxide (45% in water), mono-isopropylamine, wetter package and water were combined in the ratio 632 parts, 336 parts, 88 parts, 160 parts, and 162, parts by weight respectively to provide 1378 parts of a formulation having a density of 1.378. The wetter package was made by combining 37.5 parts S118, 4.9 parts 85% phosphoric acid and 57.6 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 151.1 |
| S118 | 60 |
| phosphoric acid | 6.66 |
| phosphoric acid-derived impurity | 1.18 |
| monoisopropylamine | 87.62 |
| water | 440 |

EXAMPLE E10

Glyphosate technical (95% purity), potassium hydroxide (45% in water), mono-isopropylamine, wetter package and water were combined in the ratio 632 parts, 336 parts, 88 parts, 160 parts, and 162 parts by weight respectively to provide 1378 parts of a formulation having a density of 1.378. The wetter package was undiluted S118. The weight composition of one liter of the final formulation was

| Component | Grams weight in 1 litre |
| --- | --- |
| glyphosate | 600.3 |
| glyphosate-derived impurity | 31.3 |
| potassium hydroxide | 151.1 |
| S118 | 160 |
| phosphoric acid | 0 |
| phosphoric acid-derived impurity | 0 |
| monoisopropylamine | 87.62 |
| water | 349 |

EXAMPLE E11

Glyphosate technical (95% purity), potassium hydroxide (45% in water), mono-isopropylamine, wetter package and water were combined in the ratio 632 parts, 336 parts, 88 parts, 160 parts, and 164 parts by weight respectively to provide 1380 parts of a formulation having a density of 1.380. The wetter package was made by combining 37.5 parts S118, 2.5 parts 85% phosphoric acid and 60 parts by weight of water. The weight composition of one liter of the final formulation was

| Component | Grams weight in 1 litre |
| --- | --- |
| glyphosate | 600.3 |
| glyphosate-derived impurity | 31.3 |
| potassium hydroxide | 151.1 |
| S118 | 60 |
| phosphoric acid | 3.4 |
| phosphoric acid-derived impurity | 0.6 |
| monoisopropylamine | 87.62 |
| water | 446 |

EXAMPLE E12

Glyphosate technical (95% purity), potassium hydroxide (45% in water), mono-isopropylamine, wetter package and water were combined in the ratio 632 parts, 448 parts, 49 parts, 160 parts, and 89 parts by weight respectively to provide 1378 parts of a formulation having a density of 1.378. The wetter package was undiluted S118. The weight composition of one liter of the final formulation was

| Component | Grams weight in 1 litre |
| --- | --- |
| glyphosate | 600.3 |
| glyphosate-derived impurity | 31.3 |
| potassium hydroxide | 201.4 |
| S118 | 160 |
| phosphoric acid | 0 |
| phosphoric acid-derived impurity | 0 |
| monoisopropylamine | 43.81 |
| water | 341 |

In the above examples, the viscosities of the formulations in cP determined on a Brookfield viscometer at 20° C. were:

E1=202, E2=122, E3=100, E4=90, E5=188, E6=172, E7=2000. Viscosity values greater than 400 were considered problematic, and values less than about 400 are considered desirable. A Brookfield viscosity reading of less than 1000 cP is considered to be a key stability indicator and an indicator of suitability for practical application. However, lower viscosities are more desirable, as centrifugal pumps used by most farmers (who are the usual end-users) begin to have problems pumping formulations with viscosities in excess 250 cP. In E8-E12 the formulations displayed crystallisation, and appropriate viscosity measurements were not possible.

Other indicators of satisfactory stability include lack of phase separation, lack of crystallization, and no jellying or solidification.

The effect of using lesser amounts of mono-ispropylamine was investigated as shown in the Examples below. Viscosity of the formulations was determined on a Brookfield viscometer at 20° C.

EXAMPLE G1

Glyphosate technical (95% purity), potassium hydroxide (45% in water), mono-isopropylamine, wetter package and water were combined in the ratio 632 parts, 510 parts, 2.5 parts, 160 parts, and 73.5 parts by weight respectively to provide 1378 parts of a formulation having a density of 1.378. The wetter package was made by combining 37.5 parts S118, 4.9 parts 85% phosphoric acid and 57.6 parts by weight of water. The weight composition of one liter of the final formulation was

| Component | Grams weight in 1 litre |
| --- | --- |
| glyphosate | 600.0 |
| Glyphosate-derived impurity | 31.6 |
| potassium hydroxide | 229.7 |
| S118 | 60 |
| phosphoric acid | 6.66 |
| phosphoric acid-derived impurity | 1.18 |
| mono-isopropylamine | 2.5 |
| water | 446.36 |

Viscosity = 80,000 cP

EXAMPLE G2

Glyphosate technical (95% purity), potassium hydroxide (45% in water), mono-isopropylamine, wetter package and water were combined in the ratio 632 parts, 504 parts, 5.0 parts, 160 parts, and 78 parts by weight respectively to provide 1379 parts of a formulation having a density of 1.379. The wetter package was made by combining 37.5 parts S118, 4.9 parts 85% phosphoric acid and 57.6 parts by weight of water. The weight composition of one liter of the final formulation was

| Component | Grams weight in 1 litre |
| --- | --- |
| glyphosate | 600.0 |
| Glyphosate-derived impurity | 31.6 |
| potassium hydroxide | 226.8 |
| S118 | 60 |
| phosphoric acid | 6.66 |
| phosphoric acid-derived impurity | 1.18 |
| mono-isopropylamine | 5.0 |
| water | 447.76 |

Viscosity = 70,000 cP

EXAMPLE G3

Glyphosate technical (95% purity), potassium hydroxide (45% in water), mono-isopropylamine, wetter package and water were combined in the ratio 632 parts, 500 parts, 7.5 parts, 160 parts, and 78.5 parts by weight respectively to provide 1378 parts of a formulation having a density of 1.378. The wetter package was made by combining 37.5 parts S118, 4.9 parts 85% phosphoric acid and 57.6 parts by weight of water. The weight composition of one liter of the final formulation was

| component | Grams weight in 1 litre |
| --- | --- |
| glyphosate | 600.0 |
| glyphosate-derived impurity | 31.6 |
| potassium hydroxide | 225.0 |
| S118 | 60 |
| phosphoric acid | 6.66 |
| phosphoric acid-derived impurity | 1.18 |
| mono-isopropylamine | 7.52 |
| water | 446.04 |

Viscosity = 73,000 cP

Summary Finding:

The ratio of potassium to MIPA glyphosate salt was varied from 99:1 (G1), through 98:2 (G2) to 97:3 (G3). All formulations were far too viscous to be marketable.

It appears that a potassium to MIPA ratio of 95.6 to 4.4 results in formulations having acceptable viscosity (example E3), and that the cut-off point is somewhere in between, say 96:4.

EXAMPLE KA1

Glyphosate technical (95% purity), potassium hydroxide (45% in water), mono-isopropylamine, wetter package and water were combined in the ratio 632 parts, 531 parts, 11 parts, 160 parts, and 47.24 parts by weight respectively to provide 1382 parts of a formulation having a density of 1.382. The wetter package was made by combining 37.5 parts S118, 9.7 parts 99.85% Acetic acid and 52.8 parts by weight of water. The weight composition of one liter of the final formulation was

| Component | Grams weight in 1 litre |
| --- | --- |
| Glyphosate | 600.2 |
| glyphosate-derived impurity | 31.6 |
| potassium hydroxide | 239.2 |
| S118 | 60 |
| Acetic acid | 15.50 |
| Acetic acid-derived impurity | 0.03 |
| Monoisopropylamine | 11 |
| Water | 424.08 |

EXAMPLE KA2

Glyphosate technical (95% purity), potassium hydroxide (45% in water), mono-isopropylamine, wetter package and water were combined in the ratio 632 parts, 531 parts, 11 parts; 160 parts, and 45.5 parts by weight respectively to provide 1380 parts of a formulation having a density of 1.380. The wetter package was made by combining 37.5 parts S118, 4.9 parts 99.85% Acetic acid and 57.6 parts by weight of water. The weight composition of one liter of the final formulation was

| Component | Grams weight in 1 litre |
| --- | --- |
| Glyphosate | 600.2 |
| glyphosate-derived impurity | 31.6 |
| potassium hydroxide | 239.2 |
| S118 | 60 |
| Acetic acid | 7.86 |
| Acetic acid-derived impurity | 0.02 |
| Monoisopropylamine | 11 |
| Water | 430.03 |

EXAMPLE KA3

Glyphosate technical (95% purity), potassium hydroxide (45% in water), mono-isopropylamine, wetter package and water were combined in the ratio 632 parts, 531 parts, 11 parts, 160 parts, and 45.7 parts by weight respectively to provide 1380 parts of a formulation having a density of 1.380. The wetter package was made by combining 37.5 parts S118, 2.5 parts 99.85% Acetic acid and 60.0 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Acetic acid | 4.06 |
| Acetic acid-derived impurity | 0.01 |
| monoisopropylamine | 11 |
| water | 434.05 |

EXAMPLE KB1

Glyphosate technical (95% purity), potassium hydroxide (45% in water), mono-isopropylamine, wetter package and water were combined in the ratio 632 parts, 531 parts, 11 parts, 160 parts, and 47.2 parts by weight respectively to provide 1381 parts of a formulation having a density of 1.381. The wetter package was made by combining 37.5 parts S118, 9.7 parts 99.9% Boric acid and 52.8 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Boric acid | 15.50 |
| Boric acid-derived impurity | 0.08 |
| monoisopropylamine | 11 |
| water | 423.98 |

EXAMPLE KB2

Glyphosate technical (95% purity), potassium hydroxide (45% in water), mono-isopropylamine, wetter package and water were combined in the ratio 632 parts, 531 parts, 11 parts, 160 parts, and 45.56 parts by weight respectively to provide 1380 parts of a formulation having a density of 1.380. The wetter package was made by combining 37.5 parts S118, 4.9 parts 99.9% Boric acid and 57.6 parts by weight of water. The weight composition of one liter of the final formulation was

| Component | Grams weight in 1 litre |
| --- | --- |
| glyphosate | 600.3 |
| glyphosate-derived impurity | 31.6 |
| potassium hydroxide | 239.2 |
| S118 | 60 |
| Boric acid | 7.88 |
| Boric acid-derived impurity | 0.04 |
| monoisopropylamine | 11 |
| water | 430.10 |

EXAMPLE KB3

Glyphosate technical (95% purity), potassium hydroxide (45% in water), mono-isopropylamine, wetter package and water were combined in the ratio 632 parts, 531 parts, 11 parts, 160 parts, and 45.72 parts by weight respectively to provide 1380 parts of a formulation having a density of 1.380. The wetter package was made by combining 37.5 parts S118, 2.5 parts 99.9% Boric acid and 60.0 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Boric acid | 4.04 |
| Boric acid-derived impurity | 0.02 |
| monoisopropylamine | 11 |
| water | 434.1 |

EXAMPLE KC1

Glyphosate technical (95% purity), potassium hydroxide (45% in water), mono-isopropylamine, wetter package and water were combined in the ratio 632 parts, 531.5 parts, 11 parts, 160 parts, and 47.29 parts by weight respectively to provide 1382 parts of a formulation having a density of 1.382. The wetter package was made by combining 37.5 parts S118, 9.7 parts 90.97% Citric acid and 52.8 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Citric acid | 13.22 |
| Citric acid-derived impurity | 2.33 |
| monoisopropylamine | 11 |
| water | 424.10 |

EXAMPLE KC2

Glyphosate technical (95% purity), potassium hydroxide (45% in water), mono-isopropylamine, wetter package and water were combined in the ratio 631.7 parts, 531.6 parts, 11 parts, 160 parts, and 45.7 parts by weight respectively to provide 1380 parts of a formulation having a density of 1.380. The wetter package was made by combining 37.5 parts S118, 4.9 parts 90.97% Citric acid and 57.6 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Citric acid | 6.71 |
| Citric acid-derived impurity | 1.18 |
| monoisopropylamine | 11 |
| water | 430.20 |

EXAMPLE KC3

Glyphosate technical (95% purity), potassium hydroxide (45% in water), mono-isopropylamine, wetter package and water were combined in the ratio 631.8 Parts, 531.5 parts, 11 parts, 160 parts, and 45.91 parts by weight respectively to provide 1380 parts of a formulation having a density of 1.380. The wetter package was made by combining 37.5 parts S118, 2.5 parts 90.97% Citric acid and 60.0 parts by weight of water. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| S118 | 60 |
| Citric acid | 3.57 |
| Citric acid-derived impurity | 0.63 |
| monoisopropylamine | 11 |
| water | 434.26 |

EXAMPLE KD1

Glyphosate technical (95% purity), potassium hydroxide (45% in water), mono-isopropylamine, wetter package and water were combined in the ratio 631.70 parts, 531.50 parts, 11 parts, 160 parts, and 47.26 parts by weight respectively to provide 1381 parts of a formulation having a density of 1.381. The wetter package was made by combining 37.5 parts S118, 9.7 parts 85% Formic acid and 52.8 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Formic acid | 14.13 |
| Formic acid-derived impurity | 1.40 |
| monoisopropylamine | 11 |
| water | 424.10 |

EXAMPLE KD2

Glyphosate technical (95% purity), potassium hydroxide (45% in water), mono-isopropylamine, wetter package and water were combined in the ratio 631.9 parts, 531.50 parts, 11 parts, 160 parts, and 45.59 parts by weight respectively to provide 1380 parts of a formulation having a density of 1.380. The wetter package was made by combining 37.5 parts S118, 4.9 parts 85% Formic acid and 57.6 parts by weight of water. The weight composition of one liter of the final formulation was

| Component | Grams weight in 1 litre |
|---|---|
| glyphosate | 600.3 |
| glyphosate-derived impurity | 31.6 |
| potassium hydroxide | 239.2 |
| S118 | 60 |
| Formic acid | 7.18 |
| Formic acid-derived impurity | 0.71 |
| monoisopropylamine | 11 |
| water | 430.10 |

EXAMPLE KD3

Glyphosate technical (95% purity), potassium hydroxide (45% in water), mono-isopropylamine, wetter package and water were combined in the ratio 631.70 parts, 531.50 parts, 11 parts, 160 parts, and 45.88 parts by weight respectively to provide 1380 parts of a formulation having a density of 1.380. The wetter package was made by combining 37.5 parts S118, 2.5 parts 85% Formic acid and 60.0 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Formic acid | 3.70 |
| Formic acid-derived impurity | 0.37 |
| monoisopropylamine | 11 |
| water | 434.20 |

EXAMPLE KE1

Glyphosate technical (95% purity), potassium hydroxide (45% in water), mono-isopropylamine, wetter package and water were combined in the ratio 631.90 parts, 531.50 parts, 11 parts, 160 parts, and 47.41 parts by weight respectively to provide 1382 parts of a formulation having a density of 1.382. The wetter package was made by combining 37.5 parts S118, 9.7 parts 32% Hydrochloric acid and 52.8 parts by weight of water. The weight composition of one liter of the final formulation was

| Component | Grams weight in 1 litre |
|---|---|
| glyphosate | 600.3 |
| glyphosate-derived impurity | 31.6 |
| potassium hydroxide | 239.2 |
| S118 | 60 |
| Hydrochloric acid | 4.98 |
| Hydrochloric acid-derived impurity | 10.58 |

| Component | Grams weight in 1 litre |
| --- | --- |
| monoisopropylamine | 11 |
| water | 424.20 |

EXAMPLE KE2

Glyphosate technical (95% purity), potassium hydroxide (45% in water), mono-isopropylamine, wetter package and water were combined in the ratio 631.90 parts, 531.60 parts, 11 parts, 160 parts, and 45.56 parts by weight respectively to provide 1380 parts of a formulation having a density of 1.380. The wetter package was made by combining 37.5 parts S118, 4.9 parts 32% Hydrochloric acid and 57.6 parts by weight of water. The weight composition of one liter of the final formulation was

| Component | Grams weight in 1 litre |
| --- | --- |
| glyphosate | 600.3 |
| glyphosate-derived impurity | 31.6 |
| potassium hydroxide | 239.2 |
| S118 | 60 |
| Hydrochloric acid | 2.53 |
| Hydrochloric acid-derived impurity | 5.37 |
| monoisopropylamine | 11 |
| water | 430.10 |

EXAMPLE KE3

Glyphosate technical (95% purity), potassium hydroxide (45% in water), mono-isopropylamine, wetter package and water were combined in the ratio 631.70 parts, 531.50 parts, 11 parts, 160 parts, and 45.73 parts by weight respectively to provide 1380 parts of a formulation having a density of 1.380. The wetter package was made by combining 37.5 parts S118, 2.5 parts 32% Hydrochloric acid and 60.0 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Hydrochloric acid | 1.29 |
| Hydrochloric acid-derived impurity | 2.74 |
| monoisopropylamine | 11 |
| water | 434.10 |

EXAMPLE KF1

Glyphosate technical (95% purity), potassium hydroxide (45% in water), mono-isopropylamine, wetter package and water were combined in the ratio 631.80 parts, 531.50 parts, 11 parts, 160 parts, and 47.22 parts by weight respectively to provide 1382 parts of a formulation having a density of 1.382. The wetter package was made by combining 37.5 parts S118, 9.7 parts 98% Phosphorous acid and 52.8 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Phosphorous acid | 15.24 |
| Phosphorous acid-derived impurity | 0.31 |
| monoisopropylamine | 11 |
| water | 424.00 |

EXAMPLE KF2

Glyphosate technical (95% purity), potassium hydroxide (45% in water), mono-isopropylamine, wetter package and water were combined in the ratio 631.80 parts, 531.50 parts, 11 parts, 160 parts, and 45.65 parts by weight respectively to provide 1380 parts of a formulation having a density of 1.380. The wetter package was made by combining 37.5 parts S118, 4.9 parts 98% Phosphorous acid and 57.6 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Phosphorous acid | 7.73 |
| Phosphorous acid-derived impurity | 0.16 |
| monoisopropylamine | 11 |
| water | 430.10 |

EXAMPLE KF3

Glyphosate technical (95% purity), potassium hydroxide (45% in water), mono-isopropylamine, wetter package and water were combined in the ratio 631.70 parts, 531 parts, 11 parts, 160 parts, and 45.78 parts by weight respectively to provide 1380 parts of a formulation having a density of 1.380. The wetter package was made by combining 37.5 parts S118, 2.5 parts 98% Phosphorous acid and 60.0 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Phosphorous acid | 4.21 |
| Phosphorous acid-derived impurity | 0.09 |
| monoisopropylamine | 11 |
| water | 434.10 |

EXAMPLE KG1

Glyphosate technical (95% purity), potassium hydroxide (45% in water), mono-isopropylamine, wetter package and water were combined in the ratio 631.70 parts, 531.50 parts, 11 parts, 160 parts, and 47.14 parts by weight respectively to provide 1381 parts of a formulation having a density of 1.381. The wetter package was made by combining 37.5 parts S118, 9.7 parts 98% Propionic acid and 52.8 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Propionic acid | 15.36 |
| Propionic acid-derived impurity | 0.16 |
| monoisopropylamine | 11 |
| water | 424.00 |

EXAMPLE KG2

Glyphosate technical (95% purity), potassium hydroxide (45% in water), mono-isopropylamine, wetter package and water were combined in the ratio 631.70 parts, 531.50 parts, 11 parts, 160 parts, and 45.48 parts by weight respectively to provide 1380 parts of a formulation having a density of 1.380. The wetter package was made by combining 37.5 parts S118, 4.9 parts 98% Propionic acid and 57.6 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Propionic acid | 7.80 |
| Propionic acid-derived impurity | 0.08 |
| monoisopropylamine | 11 |
| water | 430.00 |

EXAMPLE KG3

Glyphosate technical (95% purity), potassium hydroxide (45% in water), mono-isopropylamine, wetter package and water were combined in the ratio 631.80 parts, 531.50 parts, 11 parts, 160 parts, and 45.80 parts by weight respectively to provide 1380 parts of a formulation having a density of 1.380. The wetter package was made by combining 37.5 parts S118, 2.5 parts 98% Propionic acid and 60.0 parts by weight of water. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| S118 | 60 |
| Propionic acid | 4.19 |
| Propionic acid-derived impurity | 0.04 |
| monoisopropylamine | 11 |
| water | 434.10 |

EXAMPLE KH1

Glyphosate technical (95% purity), potassium hydroxide (45% in water), mono-isopropylamine, wetter package and water were combined in the ratio 631.70 parts, 531.50 parts, 11 parts, 160 parts, and 47.18 parts by weight respectively to provide 1381 parts of a formulation having a density of 1.381. The wetter package was made by combining 37.5 parts S118, 9.7 parts 98% Sulphuric acid and 52.8 parts by weight of water. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| S118 | 60 |
| Sulphuric acid | 15.24 |
| Sulphuric acid-derived impurity | 0.31 |
| monoisopropylamine | 11 |
| water | 424.00 |

EXAMPLE KH2

Glyphosate technical (95% purity), potassium hydroxide (45% in water), mono-isopropylamine, wetter package and water were combined in the ratio 631.80 parts, 531.50 parts, 11 parts, 160 parts, and 45.56 parts by weight respectively to provide 1380 parts of a formulation having a density of 1.380. The wetter package was made by combining 37.5 parts S118, 4.9 parts 98% Sulphuric acid and 57.6 parts by weight of water. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| S118 | 60 |
| Sulphuric acid | 7.75 |
| Sulphuric acid-derived impurity | 0.16 |
| monoisopropylamine | 11 |
| water | 430.10 |

EXAMPLE KH3

Glyphosate technical (95% purity), potassium hydroxide (45% in water), mono-isopropylamine, wetter package and water were combined in the ratio 631.60 parts, 531.50 parts, 11 parts, 160 parts, and 45.92 parts by weight respectively to provide 1380 parts of a formulation having a density of 1.380. The wetter package was made by combining 37.5 parts S118, 2.5 parts 98% Sulphuric acid and 60.0 parts by weight of water. The weight composition of one liter of the final formulation was

| Component | Grams weight in 1 litre |
|---|---|
| glyphosate | 600.0 |
| glyphosate-derived impurity | 31.6 |
| potassium hydroxide | 239.2 |
| S118 | 60 |
| Sulphuric acid | 4.13 |
| Sulphuric acid-derived impurity | 0.08 |
| monoisopropylamine | 11 |
| water | 434.30 |

EXAMPLE KI1

Glyphosate technical (95% purity), potassium hydroxide (45% in water), mono-isopropylamine, wetter package and water were combined in the ratio 631.60 parts, 531.50 parts, 11 parts, 160 parts, and 47.12 parts by weight respectively to provide 1381 parts of a formulation having a density of 1.381. The wetter package was made by combining 37.5 parts S118, 9.7 parts 50% Hypophosphorous acid and 52.8 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Hypophosphorous acid | 7.78 |
| Hypophosphorous acid-derived impurity | 7.78 |
| monoisopropylamine | 11 |
| water | 423.90 |

EXAMPLE KI2

Glyphosate technical (95% purity), potassium hydroxide (45% in water), mono-isopropylamine, wetter package and water were combined in the ratio 631.90 parts, 531.50 parts, 11 parts, 160 parts, and 45.66 parts by weight respectively to provide 1380 parts of a formulation having a density of 1.380. The wetter package was made by combining 37.5 parts S118, 4.9 parts 50% Hypophosphorous acid and 57.6 parts by weight of water. The weight composition of one liter of the final formulation was

| Component | Grams weight in 1 litre |
| --- | --- |
| glyphosate | 600.3 |
| glyphosate-derived impurity | 31.6 |
| potassium hydroxide | 239.2 |
| S118 | 60 |
| Hypophosphorous acid | 3.95 |
| Hypophosphorous acid-derived impurity | 3.95 |
| monoisopropylamine | 11 |
| water | 430.20 |

EXAMPLE KI3

Glyphosate technical (95% purity), potassium hydroxide (45% in water), mono-isopropylamine, wetter package and water were combined in the ratio 631.80 parts, 531.50 parts, 11 parts, 160 parts, and 45.92 parts by weight respectively to provide 1380 parts of a formulation having a density of 1.380. The wetter package was made by combining 37.5 parts S118, 2.5 parts 50% Hypophosphorous acid and 60.0 parts by weight of water. The weight composition of one liter of the final formulation was

| Component | Grams weight in 1 litre |
| --- | --- |
| glyphosate | 600.30 |
| glyphosate-derived impurity | 31.6 |
| potassium hydroxide | 239.2 |
| S118 | 60 |
| Hypophosphorous acid | 2.07 |
| Hypophosphorous acid-derived impurity | 2.07 |
| monoisopropylamine | 11 |
| water | 434.30 |

EXAMPLE KJ1

Glyphosate technical (95% purity), potassium hydroxide (45% in water), mono-isopropylamine, wetter package and water were combined in the ratio 631.80 parts, 531.50 parts, 11 parts, 160 parts, and 47.16 parts by weight respectively to provide 1381 parts of a formulation having a density of 1.381. The wetter package was made by combining 37.5 parts S118, 9.7 parts 94% Sodium Tripolyphosphate and 52.8 parts by weight of water. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| S118 | 60 |
| Sodium Tripolyphosphate | 14.59 |
| Sodium Tripolyphosphate-derived impurity | 0.93 |
| monoisopropylamine | 11 |
| water | 424.00 |

EXAMPLE KJ2

Glyphosate technical (95% purity), potassium hydroxide (45% in water), mono-isopropylamine, wetter package and water were combined in the ratio 631.70 parts, 531.50 parts, 11 parts, 160 parts, and 45.48 parts by weight respectively to provide 1380 parts of a formulation having a density of 1.380. The wetter package was made by combining 37.5 parts S118, 4.9 parts 94% Sodium Tripolyphosphate and 57.6 parts by weight of water. The weight composition of one liter of the final formulation was

| Component | Grams weight in 1 litre |
| --- | --- |
| glyphosate | 600.10 |
| glyphosate-derived impurity | 31.6 |
| potassium hydroxide | 239.2 |
| S118 | 60 |
| Sodium Tripolyphosphate | 7.42 |
| Sodium Tripolyphosphate-derived impurity | 0.47 |
| monoisopropylamine | 11 |
| water | 430.00 |

EXAMPLE KJ3

Glyphosate technical (95% purity), potassium hydroxide (45% in water), mono-isopropylamine, wetter package and water were combined in the ratio 631.70 parts, 531.50 parts, 11 parts, 160 parts, and 45.67 parts by weight respectively to provide 1380 parts of a formulation having a density of 1.380. The wetter package was made by combining 37.5 parts S118, 2.5 parts 94% Sodium Tripolyphosphate and 60.0 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Sodium Tripolyphosphate | 3.84 |
| Sodium Tripolyphosphate-derived impurity | 0.24 |
| monoisopropylamine | 11 |
| water | 434.00 |

EXAMPLE KK1

Glyphosate technical (95% purity), potassium hydroxide (45% in water), mono-isopropylamine, wetter package and water were combined in the ratio 631.70 parts, 53150 parts, 11 parts, 160 parts, and 47.15 parts by weight respectively to provide 1381 parts of a formulation having a density of 1.381. The wetter package was, made by combining 37.5 parts S118, 9.7 parts 95% Tetrasodium Pyrophosphate Hydrate and 52.8 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Tetrasodium Pyrophosphate Hydrate | 14.77 |
| Tetrasodium Pyrophosphate Hydrate-derived impurity | 0.78 |
| monoisopropylamine | 11 |
| water | 424.00 |

EXAMPLE KK2

Glyphosate technical (95% purity), potassium hydroxide (45% in water), mono-isopropylamine, wetter package and water were combined in the ratio 631.70 parts, 531.50 parts, 11 parts, 160 parts, and 45.82 parts by weight respectively to provide 1380 parts of a formulation having a density of 1.380. The wetter package was made by combining 37.5 parts S118, 4.9 parts 95% Tetrasodium Pyrophosphate Hydrate and 57.6 parts by weight of water. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| S118 | 60 |
| Tetrasodium Pyrophosphate Hydrate | 7.51 |
| Tetrasodium Pyrophosphate Hydrate-derived impurity | 0.40 |
| monoisopropylamine | 11 |
| water | 430.30 |

EXAMPLE KK3

Glyphosate technical (95% purity), potassium hydroxide (45% in water), mono-isopropylamine, wetter package and water were combined in the ratio 631.60 parts, 531.50 parts, 11 parts, 160 parts, and 45.62 parts by weight respectively to provide 1380 parts of a formulation having a density of 1.380. The wetter package was made by combining 37.5 parts S118, 2.5 parts 95% Tetrasodium Pyrophosphate Hydrate and 60.0 parts by weight of water. The weight composition of one liter of the final formulation was

| Component | Grams weight in 1 litre |
| --- | --- |
| glyphosate | 600.0 |
| glyphosate-derived impurity | 31.6 |
| potassium hydroxide | 239.2 |
| S118 | 60 |
| Tetrasodium Pyrophosphate Hydrate | 3.98 |
| Tetrasodium Pyrophosphate Hydrate-derived impurity | 0.21 |
| monoisopropylamine | 11 |
| water | 434.00 |

Formulations KA1, KA2, KA3, KB1, KB2, KB3, KC1, KC2, KC3, KD1, KD2, KD3, KE1, KE2, KE3, KF1, KF2, KF3, KG2, KG3, KI1, KI2, KI3, KJ1, KJ2, KJ3, KK1, KK2, and KK3 were satisfactory. They generally took the physical form of a clear amber (ranging from light to dark amber) liquid and exhibited satisfactory stability and, in most cases, viscosity. Formulations KG1, KH1, KH2, and KH3 were not satisfactory, not exhibiting satisfactory stability, either separating into two layers or forming deposits of white solid particles.

EXAMPLE LA1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1382 parts of a formulation having a density of 1.382. The wetter package was made by combining 160 parts TERWET 3780 and 15.5 parts 99.85% Acetic acid. TERWET 3780 is a surfactant substantially comprising polyethanoxy (15) tallow amine produced by Huntsman Corporation. The weight composition of one liter of the final formulation was

| Component | Grams weight in 1 litre |
| --- | --- |
| glyphosate | 600 |
| glyphosate-derived impurity | 32 |
| potassium hydroxide | 239.2 |
| TERWET 3780 | 160 |
| Acetic acid | 15.52 |
| Acetic acid-derived impurity | 0.03 |
| monoisopropylamine | 11 |
| water | 324 |

EXAMPLE LA2

Glyphosate technical (95% purity), potassium hydroxide (45% in water), mono-isopropylamine, wetter package and water were combined in the ratio 632 parts, 531 parts, 11 parts, 167.8 parts, and 38 parts by weight respectively to provide 1380 parts of a formulation having a density of 1.380. The wetter package was made by combining 160 parts TERWET 3780 and 7.8 parts 99.85% Acetic acid. The weight composition of one liter of the final formulation was

| Component | Grams weight in 1 litre |
| --- | --- |
| glyphosate | 600 |
| glyphosate-derived impurity | 32 |

| Component | Grams weight in 1 litre |
|---|---|
| potassium hydroxide | 239.2 |
| TERWET 3780 | 160 |
| Acetic acid | 7.90 |
| Acetic acid-derived impurity | 0.02 |
| monoisopropylamine | 11 |
| water | 330 |

EXAMPLE LA3

Glyphosate technical (95% purity), potassium hydroxide (45% in water), mono-isopropylamine, wetter package and water were combined in the ratio 632 parts, 531 parts, 11 parts, 164 parts, and 42 parts by weight respectively to provide 1380 parts of a formulation having a density of 1.380. The wetter package was made by combining 160 parts TERWET 3780 and 4 parts 99.85% Acetic acid. The weight composition of one liter of the final formulation was

| Component | Grams weight in 1 litre |
|---|---|
| glyphosate | 600 |
| glyphosate-derived impurity | 32 |
| potassium hydroxide | 239.2 |
| TERWET 3780 | 160 |
| Acetic acid | 4.06 |
| Acetic acid-derived impurity | 0.01 |
| monoisopropylamine | 11 |
| water | 334 |

EXAMPLE LB1

Glyphosate technical (95% purity), potassium hydroxide (45% in water), mono-isopropylamine, wetter package and water were combined in the ratio 632 parts, 531 parts, 11 parts, 175.5 parts, and 32 parts by weight respectively to provide 1382 parts of a formulation having a density of 1.382. The wetter package was made by combining 160 parts TERWET 3780 and 15.5 parts 99.9% Boric acid. The weight composition of one liter of the final formulation was

| Component | Grams weight in 1 litre |
|---|---|
| glyphosate | 600 |
| glyphosate-derived impurity | 32 |
| potassium hydroxide | 239.2 |
| TERWET 3780 | 160 |
| Boric acid | 15.46 |
| Boric acid-derived impurity | 0.08 |
| monoisopropylamine | 11 |
| water | 324 |

EXAMPLE LB2

Glyphosate technical (95% purity), potassium hydroxide (45% in water), mono-isopropylamine, wetter package and water were combined in the ratio 632 parts, 531 parts, 11 parts, 167.8 parts, and 38 parts by weight respectively to provide 1380 parts of a formulation having a density of 1.380. The wetter package was made by combining 160 parts TERWET 3780 and 7.8 parts 99.9% Boric acid. The weight composition of one liter of the final formulation was

| Component | Grams weight in 1 litre |
|---|---|
| glyphosate | 600 |
| glyphosate-derived impurity | 32 |
| potassium hydroxide | 239.2 |
| TERWET 3780 | 160 |
| Boric acid | 7.84 |
| Boric acid-derived impurity | 0.04 |
| monoisopropylamine | 11 |
| water | 330 |

EXAMPLE LB3

Glyphosate technical (95% purity), potassium hydroxide (45% in water), mono-isopropylamine, wetter package and water were combined in the ratio 632 parts, 531 parts, 11 parts, 164.02 parts, and 42 parts by weight respectively to provide 1380 parts of a formulation having a density of 1.380. The wetter package was made by combining 160 parts TERWET 3780 and 4 parts 99.9% Boric acid. The weight composition of one liter of the final formulation was

| Component | Grams weight in 1 litre |
|---|---|
| glyphosate | 600 |
| glyphosate-derived impurity | 32 |
| potassium hydroxide | 239.2 |
| TERWET 3780 | 160 |
| Boric acid | 4.00 |
| Boric acid-derived impurity | 0.00 |
| monoisopropylamine | 11 |
| water | 334.01 |

EXAMPLE LC1

Glyphosate technical (95% purity), potassium hydroxide (45% in water), mono-isopropylamine, wetter package and water were combined in the ratio 632 parts, 531 parts, 11 parts, 175.5 parts, and 32 parts by weight respectively to provide 1381 parts of a formulation having a density of 1.381. The wetter package was made by combining 160 parts TERWET 3780 and 15.5 parts 90.97% Citric acid. The weight composition of one liter of the final formulation was

| Component | Grams weight in 1 litre |
|---|---|
| glyphosate | 600 |
| glyphosate-derived impurity | 32 |
| potassium hydroxide | 239.2 |
| TERWET 3780 | 160 |
| Citric acid | 13.20 |
| Citric acid-derived impurity | 2.33 |
| monoisopropylamine | 11 |
| water | 324 |

EXAMPLE LC2

Glyphosate technical (95% purity), potassium hydroxide (45% in water), mono-isopropylamine, wetter package and water were combined in the ratio 632 parts, 531 parts, 11 parts, 167.8 parts, and 38 parts by weight respectively to provide 1380 parts of a formulation having a density of 1.380. The wetter package was made by combining 160 parts TERWET 3780 and 7.8 parts 90.97% Citric acid. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Citric acid | 6.73 |
| Citric acid-derived impurity | 1.19 |
| monoisopropylamine | 11 |
| water | 330.10 |

EXAMPLE LC3

Glyphosate technical (95% purity), potassium hydroxide (45% in water), mono-isopropylamine, wetter package and water were combined in the ratio 632 parts, 531 parts, 11 parts, 164 parts, and 42 parts by weight respectively to provide 1380 parts of a formulation having a density of 1.380. The wetter package was made by combining 160 parts TERWET 3780 and 4 parts 90.97% Citric acid. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Citric acid | 3.61 |
| Citric acid-derived impurity | 0.64 |
| monoisopropylamine | 11 |
| water | 334.20 |

EXAMPLE LD1

Glyphosate technical (95% purity), potassium hydroxide (45% in water), mono-isopropylamine, wetter package and water were combined in the ratio 632 parts, 531 parts, 11 parts, 175.5 parts, and 31.68 parts by weight respectively to provide 1381 parts of a formulation having a density of 1.381. The wetter package was made by combining 160 parts TERWET 3780 and 15.5 parts 85% Formic acid. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Formic acid | 14.15 |
| Formic acid-derived impurity | 1.40 |
| monoisopropylamine | 11 |
| water | 324.02 |

EXAMPLE LD2

Glyphosate technical (95% purity), potassium hydroxide (45% in water), mono-isopropylamine, wetter package and water were combined in the ratio 632 parts, 531 parts, 11 parts, 167.8 parts, and 38 parts by weight respectively to provide 1380 parts of a formulation having a density of 1.380. The wetter package was made by combining 160 parts TERWET 3780 and 7.8 parts 85% Formic acid. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| TERWET 3780 | 160 |
| Formic acid | 7.19 |
| Formic acid-derived impurity | 0.71 |
| monoisopropylamine | 11 |
| water | 330.09 |

EXAMPLE LD3

Glyphosate technical (95% purity), potassium hydroxide (45% in water), mono-isopropylamine, wetter package and water were combined in the ratio 632 parts, 531 parts, 11 parts, 164 parts, and 41.78 parts by weight respectively to provide 1380 parts of a formulation having a density of 1.380. The wetter package was made by combining 160 parts TERWET 3780 and 4 parts 85% Formic acid. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Formic acid | 4.0 |
| Formic acid-derived impurity | 0.4 |
| monoisopropylamine | 11 |
| water | 334 |

EXAMPLE LE1

Glyphosate technical (95% purity), potassium hydroxide (45% in water), mono-isopropylamine, wetter package and water were combined in the ratio 632 parts, 531 parts, 11 parts, 175.5 parts, and 31.62 parts by weight respectively to provide 1381 parts of a formulation having a density of 1.381. The wetter package was made by combining 160 parts TERWET 3780 and 15.5 parts 32% Hydrochloric acid. The weight composition of one liter of the final formulation was

| Component | Grams weight in 1 litre |
|---|---|
| glyphosate | 600 |
| glyphosate-derived impurity | 31.6 |
| potassium hydroxide | 239.2 |
| TERWET 3780 | 160 |
| Hydrochloric acid | 4.97 |
| Hydrochloric acid-derived impurity | 10.57 |
| monoisopropylamine | 11 |
| water | 324.00 |

EXAMPLE LE2

Glyphosate technical (95% purity), potassium hydroxide (45% in water), mono-isopropylamine, wetter package and water were combined in the ratio 632 parts, 531 parts, 11 parts, 167.9 parts, and 37.73 parts by weight respectively to provide 1380 parts of a formulation having a density of 1.380. The wetter package was made by combining 160 parts TERWET 3780 and 7.8 parts 32% Hydrochloric acid. The weight composition of one liter of the final formulation was

| Component | Grams weight in 1 litre |
|---|---|
| glyphosate | 600.2 |
| glyphosate-derived impurity | 31.59 |
| potassium hydroxide | 239.2 |
| TERWET 3780 | 160 |
| Hydrochloric acid | 2.52 |
| Hydrochloric acid-derived impurity | 5.36 |
| monoisopropylamine | 11 |
| water | 330.10 |

EXAMPLE LE3

Glyphosate technical (95% purity), potassium hydroxide (45% in water), mono-isopropylamine, wetter package and water were combined in the ratio 632 parts, 531 parts, 11 parts, 164 parts, and 41.60 parts by weight respectively to provide 1380 parts of a formulation having a density of 1.380. The wetter package was made by combining 160 parts TERWET 3780 and 4 parts 32% Hydrochloric acid. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| TERWET 3780 | 160 |
| Hydrochloric acid | 1.30 |
| Hydrochloric acid-derived impurity | 2.76 |
| monoisopropylamine | 11 |
| water | 333.94 |

EXAMPLE LF1

Glyphosate technical (95% purity), potassium hydroxide (45% in water), mono-isopropylamine, wetter package and water were combined in the ratio 632 parts, 531 parts, 11 parts, 175.5 parts, and 31.69 parts by weight respectively to provide 1381 parts of a formulation having a density of 1.381. The wetter package was made by combining 160 parts TERWET 3780 and 15.5 parts 98% Phosphorous acid. The weight composition of one liter of the final formulation was

| Component | Grams weight in 1 litre |
|---|---|
| glyphosate | 600 |
| glyphosate-derived impurity | 31.6 |
| potassium hydroxide | 239.2 |
| TERWET 3780 | 160 |
| Phosphorous acid | 15.21 |
| Phosphorous acid-derived impurity | 0.31 |
| monoisopropylamine | 11 |
| water | 324.04 |

EXAMPLE LF2

Glyphosate technical (95% purity), potassium hydroxide (45% in water), mono-isopropylamine, wetter package and water were combined in the ratio 632 parts, 531 parts, 11 parts, 167.9 parts, and 37.76 parts by weight respectively to provide 1380 parts of a formulation having a density of 1.380. The wetter package was made by combining 160 parts TERWET 3780 and 7.8 parts 98% Phosphorous acid. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Phosphorous acid | 7.72 |
| Phosphorous acid-derived impurity | 0.16 |
| monoisopropylamine | 11 |
| water | 330.11 |

EXAMPLE LF3

Glyphosate technical (95% purity), potassium hydroxide (45% in water), mono-isopropylamine, wetter package and water were combined in the ratio 632 parts, 531 parts, 11 parts, 164.1 parts, and 41.90 parts by weight respectively to provide 1380 parts of a formulation having a density of 1.380. The wetter package was made by combining 160 parts TERWET 3780 and 4 parts 98% Phosphorous acid. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| TERWET 3780 | 160 |
| Phosphorous acid | 3.98 |
| Phosphorous acid-derived impurity | 0.08 |
| monoisopropylamine | 11 |
| water | 334.29 |

EXAMPLE LG1

Glyphosate technical (95% purity), potassium hydroxide (45% in water), mono-isopropylamine, wetter package and water were combined in the ratio 632 parts, 531.50 parts, 11 parts, 175.5 parts, and 31.72 parts by weight respectively to provide 1382 parts of a formulation having a density of 1.382. The wetter package was made by combining 160 parts TERWET 3780 and 15.5 parts 98% Propionic acid. The weight composition of one liter of the final formulation was

| Component | Grams weight in 1 litre |
|---|---|
| glyphosate | 600.2 |
| glyphosate-derived impurity | 31.6 |
| potassium hydroxide | 239.2 |
| TERWET 3780 | 160 |
| Propionic acid | 15.36 |
| Propionic acid-derived impurity | 0.16 |
| monoisopropylamine | 11 |
| water | 324.10 |

EXAMPLE LG2

Glyphosate technical (95% purity), potassium hydroxide (45% in water), mono-isopropylamine, wetter package and water were combined in the ratio 632 parts, 531.55 parts, 11 parts, 167.8 parts, and 37.63 parts by weight respectively to provide 1380 parts of a formulation having a density of 1.380. The wetter package was made by combining 160 parts TERWET 3780 and 7.8 parts 98% Propionic acid. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Propionic acid | 7.82 |
| Propionic acid-derived impurity | 0.08 |
| monoisopropylamine | 11 |
| water | 329.99 |

EXAMPLE LG3

Glyphosate technical (95% purity), potassium hydroxide (45% in water), mono-isopropylamine, wetter package and water were combined in the ratio 632 parts, 531.52 parts, 11 parts, 164 parts, and 41.85 parts by weight respectively to provide 1380 parts of a formulation having a density of 1.380. The wetter package was made by combining 160 parts TERWET 3780 and 4 parts 98% Propionic acid. The weight composition of one liter of the final formulation was

| Component | Grams weight in 1 litre |
| --- | --- |
| glyphosate | 600.4 |
| glyphosate-derived impurity | 31.6 |
| potassium hydroxide | 239.2 |
| TERWET 3780 | 160 |
| Propionic acid | 4.01 |
| Propionic acid-derived impurity | 0.04 |
| monoisopropylamine | 11 |
| water | 334.19 |

EXAMPLE LH1

Glyphosate technical (95% purity), potassium hydroxide (45% in water), mono-isopropylamine, wetter package and water were combined in the ratio 632 parts, 531.54 parts, 11 parts, 175.5 parts, and 31.81 parts by weight respectively to provide 1382 parts of a formulation having a density of 1.382. The wetter package was made by combining 160 parts TERWET 3780 and 15.5 parts 98% Sulphuric acid. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Sulphuric acid | 15.23 |
| Sulphuric acid-derived impurity | 0.31 |
| monoisopropylamine | 11 |
| water | 324.16 |

EXAMPLE LH2

Glyphosate technical (95% purity), potassium hydroxide (45% in water), mono-isopropylamine, wetter package and water were combined in the ratio 632 parts, 531.56 parts, 11 parts, 167.9 parts, and 37.74 parts by weight respectively to provide 1380 parts of a formulation having a density of 1.380. The wetter package was made by combining 160 parts TERWET 3780 and 7.8 parts 98% Sulphuric acid. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Sulphuric acid | 7.75 |
| Sulphuric acid-derived impurity | 0.16 |
| monoisopropylamine | 11 |
| water | 330.10 |

EXAMPLE LH3

Glyphosate technical (95% purity), potassium hydroxide (45% in water), mono-isopropylamine, wetter package and water were combined in the ratio 632 parts, 531.56 parts, 11 parts, 164.10 parts, and 41.83 parts by weight respectively to provide 1380 parts of a formulation having a density of 1.380. The wetter package was made by combining 160 parts TERWET 3780 and 4 parts 98% Sulphuric acid. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| TERWET 3780 | 160 |
| Sulphuric acid | 4.06 |
| Sulphuric acid-derived impurity | 0.08 |
| monoisopropylamine | 11 |
| water | 334.20 |

EXAMPLE LI1

Glyphosate technical (95% purity), potassium hydroxide (45% in water), mono-isopropylamine, wetter package and water were combined in the ratio 632 parts, 531 parts, 11 parts, 175.6 parts, and 31.66 parts by weight respectively to provide 1381 parts of a formulation having a density of 1.381. The wetter package was made by combining 160 parts TERWET 3780 and 15.5 parts 50% Hypophosphorous acid. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Hypophosphorous acid | 7.78 |
| Hypophosphorous acid-derived impurity | 7.78 |
| monoisopropylamine | 11 |
| water | 324.00 |

EXAMPLE LI2

Glyphosate technical (95% purity), potassium hydroxide (45% in water), mono-isopropylamine, wetter package and water were combined in the ratio 632 parts, 531.53 parts, 11 parts, 167.9 parts, and 37.74 parts by weight respectively to provide 1380 parts of a formulation having a density of 1.380. The wetter package was made by combining 160 parts TERWET 3780 and 7.8 parts 50% Hypophosphorous acid. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| TERWET 3780 | 160 |
| Hypophosphorous acid | 3.95 |
| Hypophosphorous acid-derived impurity | 3.95 |
| monoisopropylamine | 11 |
| water | 330.10 |

EXAMPLE LI3

Glyphosate technical (95% purity), potassium hydroxide (45% in water), mono-isopropylamine, wetter package and water were combined in the ratio 632 parts, 531.52 parts, 11 parts, 164 parts, and 41.88 parts by weight respectively to provide 1380 parts of a formulation having a density of 1.380. The wetter package was made by combining 160 parts TERWET 3780 and 4 parts 50% Hypophosphorous acid. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Hypophosphorous acid | 2.01 |
| Hypophosphorous acid-derived impurity | 2.01 |
| monoisopropylamine | 11 |
| water | 334.20 |

EXAMPLE LJ1

Glyphosate technical (95% purity), potassium hydroxide (45% in water), mono-isopropylamine, wetter package and water were combined in the ratio 631.7 parts, 531.53 parts, 11 parts, 175.5 parts, and 31.70 parts by weight respectively to provide 1381 parts of a formulation having a density of 1.381. The wetter package was made by combining 160 parts TERWET 3780 and 15.5 parts 94% Sodium Tripolyphosphate. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Sodium Tripolyphosphate | 14.60 |
| Sodium Tripolyphosphate-derived impurity | 0.93 |
| monoisopropylamine | 11 |
| water | 324.00 |

EXAMPLE LJ2

Glyphosate technical (95% purity), potassium hydroxide (45% in water), mono-isopropylamine, wetter package and water were combined in the ratio 632 parts, 531.55 parts, 11 parts, 167.9 parts, and 37.87 parts by weight respectively to provide 1380 parts of a formulation having a density of 1.380. The wetter package was made by combining 160 parts TERWET 3780 and 7.8 parts 94% Sodium Tripolyphosphate. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Sodium Tripolyphosphate | 7.42 |
| Sodium Tripolyphosphate-derived impurity | 0.47 |
| monoisopropylamine | 11 |
| water | 330.23 |

EXAMPLE LJ3

Glyphosate technical (95% purity), potassium hydroxide (45% in water), mono-isopropylamine, wetter package and water were combined in the ratio 632 parts, 531.54 parts, 11 parts, 164 parts, and 41.76 parts by weight respectively to provide 1380 parts of a formulation having a density of 1.380. The wetter package was made by combining 160 parts TERWET 3780 and 4 parts 94% Sodium Tripolyphosphate. The weight composition of one liter of the final formulation was

| Component | Grams weight in 1 litre |
| --- | --- |
| glyphosate | 600.2 |
| glyphosate-derived impurity | 31.6 |
| potassium hydroxide | 239.2 |
| TERWET 3780 | 160 |
| Sodium Tripolyphosphate | 3.82 |
| Sodium Tripolyphosphate-derived impurity | 0.24 |
| monoisopropylamine | 11 |
| water | 334.10 |

EXAMPLE LK1

Glyphosate technical (95% purity), potassium hydroxide (45% in water), mono-isopropylamine, wetter package and water were combined in the ratio 632 parts, 531 parts, 11 parts, 175.5 parts, and 31.70 parts by weight respectively to provide 1381 parts of a formulation having a density of 1.381. The wetter package was made by combining 160 parts TERWET 3780 and 15.5 parts 95% Tetrasodium Pyrophosphate Hydrate. The weight composition of one liter of the final formulation was

| Component | Grams weight in 1 litre |
| --- | --- |
| glyphosate | 600.1 |
| glyphosate-derived impurity | 31.6 |
| potassium hydroxide | 239.2 |
| TERWET 3780 | 160 |
| Tetrasodium Pyrophosphate Hydrate | 14.76 |
| Tetrasodium Pyrophosphate Hydrate-derived impurity | 0.78 |
| monoisopropylamine | 11 |
| water | 324.04 |

EXAMPLE LK2

Glyphosate technical (95% purity), potassium hydroxide (45% in water), mono-isopropylamine, wetter package and water were combined in the ratio 632 parts, 531.53 parts; 11 parts, 167.9 parts, and 37.74 parts by weight respectively to provide 1380 parts of a formulation having a density of 1.380. The wetter package was made by combining 160 parts TER- WET 3780 and 7.8 parts 95% Tetrasodium Pyrophosphate Hydrate. The weight composition of one liter of the final formulation was

| Component | Grams weight in 1 litre |
|---|---|
| glyphosate | 600.1 |
| glyphosate-derived impurity | 31.6 |
| potassium hydroxide | 239.2 |
| TERWET 3780 | 160 |
| Tetrasodium Pyrophosphate Hydrate | 7.50 |
| Tetrasodium Pyrophosphate Hydrate-derived impurity | 0.39 |
| monoisopropylamine | 11 |
| water | 330.08 |

EXAMPLE LK3

Glyphosate technical (95% purity), potassium hydroxide (45% in water), mono-isopropylamine, wetter package and water were combined in the ratio 632 parts, 531.52 parts, 11 parts, 164.20 parts, and 41.67 parts by weight respectively to provide 1380 parts of a formulation having a density of 1.380. The wetter package was made by combining 160 parts TERWET 3780 and 4 parts 95% Tetrasodium Pyrophosphate Hydrate. The weight composition of one liter of the final formulation was

| Component | Grams weight in 1 litre |
|---|---|
| glyphosate | 600.3 |
| glyphosate-derived impurity | 31.6 |
| potassium hydroxide | 239.2 |
| TERWET 3780 | 160 |
| Tetrasodium Pyrophosphate Hydrate | 4.02 |
| Tetrasodium Pyrophosphate Hydrate-derived impurity | 0.21 |
| monoisopropylamine | 11 |
| water | 334.00 |

Formulations LA1 to LK3 were all unsatisfactory. All exhibited separation into two layers due to incompatibility of the glyphosate mix and surfactant.

EXAMPLE MA1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 99.85% Acetic acid. GERONOL CFAS30HL is a surfactant substantially comprised of quaternary ammonium compounds produced by Rhodia. The weight composition of one liter of the final formulation was

| Component | Grams weight in 1 litre |
|---|---|
| Glyphosate | 600 |
| glyphosate-derived impurity | 32 |
| potassium hydroxide | 239.4 |
| GERONOL CFAS30HL | 160 |
| Acetic acid | 15.50 |
| Acetic acid-derived impurity | 0.03 |
| Monoisopropylamine | 11 |
| Water | 324.60 |

EXAMPLE MA2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 99.85% Acetic acid. The weight composition of one liter of the final formulation was

| Component | Grams weight in 1 litre |
|---|---|
| Glyphosate | 600.1 |
| glyphosate-derived impurity | 32 |
| potassium hydroxide | 239.4 |
| GERONOL CFAS30HL | 160 |
| Acetic acid | 7.88 |
| Acetic acid-derived impurity | 0.02 |
| monoisopropylamine | 11 |
| water | 330.6 |

EXAMPLE MA3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 99.85% Acetic acid. The weight composition of one liter of the final formulation was

| Component | Grams weight in 1 litre |
|---|---|
| Glyphosate | 600.1 |
| glyphosate-derived impurity | 32 |
| potassium hydroxide | 239.4 |
| GERONOL CFAS30HL | 160 |
| Acetic acid | 4.07 |
| Acetic acid-derived impurity | 0.01 |
| monoisopropylamine | 11 |
| water | 334.60 |

EXAMPLE MB1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 99.9% Boric acid. The weight composition of one liter of the final formulation was

| Component | Grams weight in 1 litre |
|---|---|
| glyphosate | 600.1 |
| glyphosate-derived impurity | 32 |
| potassium hydroxide | 239.4 |
| GERONOL CFAS30HL | 160 |
| Boric acid | 15.46 |
| Boric acid-derived impurity | 0.08 |
| monoisopropylamine | 11 |
| water | 324.60 |

EXAMPLE MB2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 99.9% Boric acid. The weight composition of one liter of the final formulation was

| Component | Grams weight in 1 litre |
| --- | --- |
| Glyphosate | 600.2 |
| glyphosate-derived impurity | 32 |
| potassium hydroxide | 239.4 |
| GERONOL CFAS30HL | 160 |
| Boric acid | 7.86 |
| Boric acid-derived impurity | 0.04 |
| monoisopropylamine | 11 |
| water | 330.60 |

EXAMPLE MB3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 99.9% Boric acid. The weight composition of one liter of the final formulation was

| Component | Grams weight in 1 litre |
| --- | --- |
| glyphosate | 600.2 |
| glyphosate-derived impurity | 32 |
| potassium hydroxide | 239.4 |
| GERONOL CFAS30HL | 160 |
| Boric acid | 4.20 |
| Boric acid-derived impurity | 0.02 |
| monoisopropylamine | 11 |
| water | 334.60 |

EXAMPLE MC1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 90.97% Citric acid. The weight composition of one liter of the final formulation was

| Component | Grams weight in 1 litre |
| --- | --- |
| glyphosate | 600.2 |
| glyphosate-derived impurity | 32 |
| potassium hydroxide | 239.4 |
| GERONOL CFAS30HL | 160 |
| Citric acid | 13.2 |
| Citric acid-derived impurity | 2.33 |
| monoisopropylamine | 11 |
| water | 324.60 |

EXAMPLE MC2

Glyphosate technical (95% purity), potassium hydroxide (45% in water), mono-isopropylamine, wetter package and water were combined in the ratio 632 parts, 532 parts, 11 parts, 167.8 parts, and 38 parts by, weight respectively to provide 1381 parts of a formulation having a density of 1.381. The wetter package was made by combining 160 parts GERONOL CFAS30HL and 7.8 parts 90.97% Citric acid. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Citric acid | 6.70 |
| Citric acid-derived impurity | 1.18 |
| monoisopropylamine | 11 |
| water | 330.60 |

EXAMPLE MC3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 90.97% Citric acid. The weight composition of one liter of the final formulation was

| Component | Grams weight in 1 litre |
| --- | --- |
| Glyphosate | 600 |
| glyphosate-derived impurity | 32 |
| potassium hydroxide | 239.4 |
| GERONOL CFAS30HL | 160 |
| Citric acid | 3.70 |
| Citric acid-derived impurity | 0.65 |
| monoisopropylamine | 11 |
| water | 334.60 |

EXAMPLE MD1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 85% Formic acid. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Formic acid | 14.15 |
| Formic acid-derived impurity | 1.40 |
| monoisopropylamine | 11 |
| water | 324.60 |

EXAMPLE MD2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 85% Formic acid. The weight composition of one liter of the final formulation was

| Component | Grams weight in 1 litre |
|---|---|
| Glyphosate | 600.1 |
| glyphosate-derived impurity | 32 |
| potassium hydroxide | 239.4 |
| GERONOL CFAS30HL | 160 |
| Formic acid | 7.18 |
| Formic acid-derived impurity | 0.71 |
| monoisopropylamine | 11 |
| water | 330.60 |

EXAMPLE MD3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 85% Formic acid. The weight composition of one liter of the final formulation was

| Component | Grams weight in 1 litre |
|---|---|
| Glyphosate | 600.3 |
| glyphosate-derived impurity | 32 |
| potassium hydroxide | 239.4 |
| GERONOL CFAS30HL | 160 |
| Formic acid | 3.84 |
| Formic acid-derived impurity | 0.38 |
| monoisopropylamine | 11 |
| water | 334.60 |

EXAMPLE ME1

Glyphosate technical (95% purity), potassium hydroxide (45% in water), mono-isopropylamine, wetter package and water were combined, in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 32% Hydrochloric acid. The weight composition of one liter of the final formulation was

| Component | Grams weight in 1 litre |
|---|---|
| glyphosate | 600.3 |
| glyphosate-derived impurity | 32 |
| potassium hydroxide | 239.4 |
| GERONOL CFAS30HL | 160 |
| Hydrochloric acid | 4.98 |
| Hydrochloric acid-derived impurity | 10.57 |
| monoisopropylamine | 11 |
| water | 324.60 |

EXAMPLE ME2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 32% Hydrochloric acid. The weight composition of one liter of the final formulation was

| Component | Grams weight in 1 litre |
|---|---|
| glyphosate | 600.3 |
| glyphosate-derived impurity | 32 |
| potassium hydroxide | 239.4 |
| GERONOL CFAS30HL | 160 |
| Hydrochloric acid | 2.53 |
| Hydrochloric acid-derived impurity | 5.38 |
| monoisopropylamine | 11 |
| water | 330.60 |

EXAMPLE ME3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 32% Hydrochloric acid. The weight composition of one liter of the final formulation was

| Component | Grams weight in 1 litre |
|---|---|
| Glyphosate | 600 |
| glyphosate-derived impurity | 32 |
| potassium hydroxide | 239.4 |
| GERONOL CFAS30HL | 160 |
| Hydrochloric acid | 1.32 |
| Hydrochloric acid-derived impurity | 2.80 |
| monoisopropylamine | 11 |
| water | 334.60 |

EXAMPLE MF1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 98% Phosphorous acid. The weight composition of one liter of the final formulation was

| Component | Grams weight in 1 litre |
|---|---|
| Glyphosate | 600.3 |
| glyphosate-derived impurity | 32 |
| potassium hydroxide | 239.4 |
| GERONOL CFAS30HL | 160 |
| Phosphorous acid | 15.22 |
| Phosphorous acid-derived impurity | 0.31 |
| monoisopropylamine | 11 |
| water | 324.60 |

EXAMPLE MF2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 98% Phosphorous acid. The weight composition of one liter of the final formulation was

| Component | Grams weight in 1 litre |
| --- | --- |
| glyphosate | 600.2 |
| glyphosate-derived impurity | 32 |
| potassium hydroxide | 239.4 |
| GERONOL CFAS30HL | 160 |
| Phosphorous acid | 7.73 |
| Phosphorous acid-derived impurity | 0.16 |
| monoisopropylamine | 11 |
| water | 330.60 |

EXAMPLE MF3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 98% Phosphorous acid. The weight composition of one liter of the final formulation was

| Component | Grams weight in 1 litre |
| --- | --- |
| Glyphosate | 600.3 |
| glyphosate-derived impurity | 32 |
| potassium hydroxide | 239.4 |
| GERONOL CFAS30HL | 160 |
| Phosphorous acid | 3.93 |
| Phosphorous acid-derived impurity | 0.08 |
| monoisopropylamine | 11 |
| water | 334.60 |

EXAMPLE MG1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 98% Propionic acid. The weight composition of one liter of the final formulation was

| Component | Grams weight in 1 litre |
| --- | --- |
| Glyphosate | 600 |
| glyphosate-derived impurity | 32 |
| potassium hydroxide | 239.4 |
| GERONOL CFAS30HL | 160 |
| Propionic acid | 15.39 |
| Propionic acid-derived impurity | 0.16 |
| monoisopropylamine | 11 |
| water | 324.60 |

EXAMPLE MG2

Glyphosate technical (95% purity), potassium hydroxide (45% in water), mono-isopropylamine, wetter package and water were combined in the ratio 632 parts; 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 98% Propionic acid. The weight composition of one liter of the final formulation was

| Component | Grams weight in 1 litre |
| --- | --- |
| glyphosate | 600.2 |
| glyphosate-derived impurity | 32 |
| potassium hydroxide | 239.4 |
| GERONOL CFAS30HL | 160 |
| Propionic acid | 7.81 |
| Propionic acid-derived impurity | 0.08 |
| monoisopropylamine | 11 |
| water | 330.60 |

EXAMPLE MG3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 98% Propionic acid. The weight composition of one liter of the final formulation was

| Component | Grams weight in 1 litre |
| --- | --- |
| glyphosate | 600 |
| glyphosate-derived impurity | 32 |
| potassium hydroxide | 239.4 |
| GERONOL CFAS30HL | 160 |
| Propionic acid | 4.16 |
| Propionic acid-derived impurity | 0.04 |
| monoisopropylamine | 11 |
| water | 334.60 |

EXAMPLE MH1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 98% Sulphuric acid. The weight composition of one liter of the final formulation was

| Component | Grams weight in 1 litre |
| --- | --- |
| Glyphosate | 600.2 |
| glyphosate-derived impurity | 32 |
| potassium hydroxide | 239.4 |
| GERONOL CFAS30HL | 160 |
| Sulphuric acid | 15.22 |
| Sulphuric acid-derived impurity | 0.31 |
| monoisopropylamine | 11 |
| water | 324.60 |

EXAMPLE MH2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 98% Sulphuric acid. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Sulphuric acid | 7.73 |
| Sulphuric acid-derived impurity | 0.16 |
| monoisopropylamine | 11 |
| water | 330.60 |

EXAMPLE MH3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 98% Sulphuric acid. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Sulphuric acid | 3.99 |
| Sulphuric acid-derived impurity | 0.08 |
| monoisopropylamine | 11 |
| water | 334.60 |

EXAMPLE MI1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 50% Hypophosphorous acid. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Hypophosphorous acid | 7.77 |
| Hypophosphorous acid-derived impurity | 7.77 |
| monoisopropylamine | 11 |
| water | 324.60 |

EXAMPLE MI2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 50% Hypophosphorous acid. The weight composition of one liter of the final formulation was

| Component | Grams weight in 1 litre |
| --- | --- |
| glyphosate | 600.1 |
| glyphosate-derived impurity | 32 |
| potassium hydroxide | 239.4 |
| GERONOL CFAS30HL | 160 |
| Hypophosphorous acid | 3.95 |
| Hypophosphorous acid-derived impurity | 3.95 |
| monoisopropylamine | 11 |
| water | 330.60 |

EXAMPLE MI3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 50% Hypophosphorous acid. The weight composition of one liter of the final formulation was

| Component | Grams weight in 1 litre |
| --- | --- |
| Glyphosate | 600.2 |
| glyphosate-derived impurity | 32 |
| potassium hydroxide | 239.4 |
| GERONOL CFAS30HL | 160 |
| Hypophosphorous acid | 2.07 |
| Hypophosphorous acid-derived impurity | 2.07 |
| monoisopropylamine | 11 |
| water | 334.60 |

EXAMPLE MJ1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 94% Sodium Tripolyphosphate. The weight composition of one liter of the final formulation was

| Component | Grams weight in 1 litre |
| --- | --- |
| Glyphosate | 600.1 |
| glyphosate-derived impurity | 32 |
| potassium hydroxide | 239.4 |
| GERONOL CFAS30HL | 160 |
| Sodium Tripolyphosphate | 14.62 |
| Sodium Tripolyphosphate-derived impurity | 0.93 |

EXAMPLE MJ2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 94% Sodium Tripolyphosphate. The weight composition of one liter of the final formulation was

| Component | Grams weight in 1 litre |
|---|---|
| monoisopropylamine | 11 |
| water | 324.60 |

| Component | Grams weight in 1 litre |
|---|---|
| Glyphosate | 600.1 |
| glyphosate-derived impurity | 32 |
| potassium hydroxide | 239.4 |
| GERONOL CFAS30HL | 160 |
| Sodium Tripolyphosphate | 7.43 |
| Sodium Tripolyphosphate-derived impurity | 0.47 |
| monoisopropylamine | 11 |
| water | 330.60 |

EXAMPLE MJ3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 94% Sodium Tripolyphosphate. The weight composition of one liter of the final formulation was

| Component | Grams weight in 1 litre |
|---|---|
| glyphosate | 600.1 |
| glyphosate-derived impurity | 32 |
| potassium hydroxide | 239.4 |
| GERONOL CFAS30HL | 160 |
| Sodium Tripolyphosphate | 3.84 |
| Sodium Tripolyphosphate-derived impurity | 0.24 |
| monoisopropylamine | 11 |
| water | 334.60 |

EXAMPLE MK1

Glyphosate technical (95% purity), potassium hydroxide (45% in water), mono-isopropylamine, wetter package and water were combined in the ratio 632 parts, 532 parts, 11 parts, 175.5 parts, and 32 parts by weight respectively to provide 1383 parts of a formulation having a density of 1.383. The wetter package was made by combining 160 parts GERONOL CFAS30HL and 15.5 parts 95% Tetrasodium Pyrophosphate Hydrate. The weight composition of one liter of the final formulation was

| Component | Grams weight in 1 litre |
|---|---|
| glyphosate | 600.1 |
| glyphosate-derived impurity | 32 |
| potassium hydroxide | 239.4 |
| GERONOL CFAS30HL | 160 |
| Tetrasodium Pyrophosphate Hydrate | 14.76 |
| Tetrasodium Pyrophosphate Hydrate-derived impurity | 0.78 |
| monoisopropylamine | 11 |
| water | 324.60 |

EXAMPLE MK2

Glyphosate technical (95% purity), potassium hydroxide (45% in water), mono-isopropylamine, wetter package and water were combined in the ratio 632 parts, 532 parts, 11 parts, 167.8 parts, and 38 parts by weight respectively to provide 1381 parts of a formulation having a density of 1.381. The wetter package was made by combining 160 parts GERONOL CFAS30HL and 7.8 parts 95% Tetrasodium Pyrophosphate Hydrate. The weight composition of one liter of the final formulation was

| Component | Grams weight in 1 litre |
|---|---|
| glyphosate | 600 |
| glyphosate-derived impurity | 32 |
| potassium hydroxide | 239.4 |
| GERONOL CFAS30HL | 160 |
| Tetrasodium Pyrophosphate Hydrate | 7.50 |
| Tetrasodium Pyrophosphate Hydrate-derived impurity | 0.39 |
| monoisopropylamine | 11 |
| water | 330.60 |

EXAMPLE MK3

Glyphosate technical (95% purity), potassium hydroxide (45% in water), mono-isopropylamine, wetter package and water were combined in the ratio 632 parts, 532 parts, 11 parts, 164 parts, and 42 parts by weight respectively to provide 1381 parts of a formulation having a density of 1.381. The wetter package was made by combining 160 parts GERONOL CFAS30HL and 4 parts 95% Tetrasodium Pyrophosphate Hydrate. The weight composition of one liter of the final formulation was

| Component | Grams weight in 1 litre |
|---|---|
| glyphosate | 600.3 |
| glyphosate-derived impurity | 32 |
| potassium hydroxide | 239.4 |
| GERONOL CFAS30HL | 160 |
| Tetrasodium Pyrophosphate Hydrate | 3.83 |
| Tetrasodium Pyrophosphate Hydrate-derived impurity | 0.20 |
| monoisopropylamine | 11 |
| water | 334.60 |

Formulations MA1 to MK3 were all unsatisfactory. All exhibited the formation of two layers with the top layer comprising a gelatinous liquid and the bottom layer comprising a clear liquid.

EXAMPLE N1

Glyphosate technical (95% purity), potassium hydroxide (48% in water), mono-isopropylamine, wetter, anti-foaming agent and water were combined in the ratio 658 parts, 227.24 parts, 56.40 parts, 166.40 parts, 1.20 parts and 290 parts by weight respectively to provide 1399 parts of a formulation having a density of 1.399. The wetter package was made by combining 37.5 parts S118, 9.7 parts 85% phosphoric acid and 52.8 parts by weight of water. S118 is amidoamine surfactant substantially comprising of cocoamidopropyl dimethyl amine. The weight composition of one liter of the final formulation was

| Component | Grams weight in 1 litre |
|---|---|
| Glyphosate | 625.23 |
| Glyphosate-derived impurity | 32.91 |
| Potassium hydroxide | 227.24 |
| S118 | 62.40 |
| Phosphoric acid | 13.72 |
| Phosphoric acid-derived impurity | 2.42 |
| Monoisopropylamine | 56.40 |
| Water | 377.86 |
| Rhodoline 5888 | 1.20 |
| Sunset Yellow Dye | 0.01 |

This formulation met stability and viscosity requirements and was satisfactory.

The descriptions of the embodiments and examples referred to above are for the purposes of illustrating the nature of the invention by way of preferments and are not intended to be limiting on the scope of the invention as described and claimed.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Reference to any prior art in this specification is not, and should not be taken as, an acknowledgment or any form or suggestion that the prior art forms part of the common general knowledge in Australia or elsewhere.

The invention claimed is:
1. A stable liquid formulation containing:
   (a) at least or about 570 ae g/L of glyphosate;
   (b) an amido-amine or ester-amine surfactant that is efficacy-enhancing for glyphosate and is compatible with potassium glyphosate and which is present at less than or about 100 g/L of the formulation, said surfactant being:
      (i) selected from the group consisting of amino compounds with the formula:

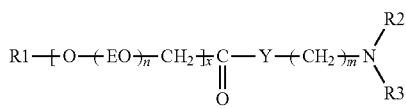

where R1 is an aliphatic group containing 7-22 carbon atoms; EO is an ethyleneoxy group; Y is O or NH; R2 and R3 is independently $-CH_2CH_2OH$, $-CH_2CH(CH_3)OH$, or an alkyl group with 1-5 carbon atoms; n is a number between 0-10; x is a number 0 or 1 provided that when Y is O, then x is 1, and when Y is NH, then x is 0; and m is a number 2-6 provided that when Y is NH, then m is 3-6; or an adduct obtained by reacting one mole of the compound with 1-5 moles of an alkylene oxide having 2-3 carbon atoms;

(ii) an amido-amine compound obtained by a reaction between a fatty acid or a fatty acid methyl ester and a diamine; or
   (iii) an ester-amine compound obtained from a ethoxylated alcohol that has been carboxymethylated, and then esterified with a tertiary hydroxyamine;
   (c) non-amphiphilic cations, wherein said non-amphiphilic cations are potassium and iso-propylammonium in a mole ratio of between 96:4 and 80:20;
   (d) at least one low molecular weight acid or conjugate base of a low molecular weight acid that is chemically distinct from glyphosate, wherein said low molecular weight acid or conjugate base thereof has a molecular weight of less than or about 1000;
   (e) water; and
   (f) wherein said surfactant being conditioned prior to its incorporation into the formulation by the addition of the low molecular weight acid or conjugate base thereof to the surfactant.

2. A liquid formulation as claimed in claim 1 containing at least or about 600 ae g/L of glyphosate.

3. A liquid formulation as claimed in claim 1 wherein said surfactant that is efficacy-enhancing glyphosate is present at less than or about 70 g/L in the formulation.

4. A liquid formulation as claimed in claim 1 wherein said surfactant is selected from the group of amido-amine surfactants.

5. A liquid formulation as claimed in claim 1 wherein said surfactant is selected from the group R1-amidopropylamino-R2,R3, where R1 is selected from the group comprising branched or straight C8-C18 alkyl radicals, and R2,R3 are independently chosen from branched or straight C2-C8 alkyl radicals.

6. A liquid formulation as claimed in claim 1 wherein said surfactant is selected from the group R1-amidopropyl amino-R2,R3, where R1 is selected from the group comprising branched or straight C8-C18 alkyl radicals, and R2,R3 are independently chosen from branched or straight C1-C4 alkyl radicals.

7. A liquid formulation as claimed in claim 1 wherein said surfactant comprises coco amidopropyl dimethylamine moieties.

8. A liquid formulation as claimed in claim 1 containing at least or about 400 g/L of water.

9. A liquid formulation as claimed in claim 1 wherein said formulation contains at least or about 377 g/L of water.

10. A liquid formulation as claimed in claim 1 wherein said low molecular weight acid or conjugate base thereof is derived from moieties in the set consisting of acetic acid, boric acid, citric acid, formic acid, hydrochloric acid, phosphoric acid, phosphorous acid, propionic acid, hypophosphorous acid, sodium tripolyphosphate or another salt of tripolyphosphate, tetrasodium pyrophosphate or another salt of pyrophosphate.

11. A liquid formulation as claimed in claim 1 wherein said low molecular weight acid or conjugate base thereof has a molecular weight of less than or about 300.

12. A liquid formulation as claimed in claim 1 wherein said low molecular weight acid is phosphoric acid.

13. A liquid formulation as claimed in claim 1 wherein said surfactant is conditioned by the addition of a low molecular weight acid or conjugate base thereof to the surfactant.

14. A liquid formulation as claimed in claim 1 wherein said surfactant is conditioned by the addition of water as well as a low molecular weight acid or conjugate base thereof to the surfactant.

15. A liquid formulation as claimed in claim 14 wherein said surfactant that is efficacy-enhancing for glyphosate is conditioned by taking one part by weight of said surfactant and mixing together with between 0.2 and 3 parts of water and 0.01 and 0.5 parts of phosphoric acid.

16. A liquid formulation as claimed in claim 1 wherein the liquid formulation has a viscosity of 1000 cP or less as determined on a Brookfield viscometer at 20° C.

17. A liquid formulation as claimed in claim 1 wherein said viscosity is 500 cP or less as determined on a Brookfield viscometer at 20° C.

18. A liquid formulation as claimed in claim 1 wherein said viscosity is 250 cP or less as determined on a Brookfield viscometer at 20° C.

19. A method for preparing a stable liquid formulation of claim 1 comprising the steps of:
   a) preparing a wetter package by combining: (i) at least one low molecular weight acid or conjugate base of a low molecular weight acid that is chemically distinct from glyphosate with a molecular weight of less than about 1000 with (ii) a surfactant that is efficacy-enhancing for glyphosate and is compatible with potassium glyphosate and which constitutes less than about 100 g/L of the formulation, said surfactant being selected from the group including amido-amine surfactants and ester-amine surfactants preparing an admixture of; and
   (b) combining the wetter package with (i) at least or about 570 ae g/L of glyphosate; (ii) non-amphiphilic cations, wherein said non-amphiphilic cations are potassium and iso-propylammonium in a mole ratio of between 96:4 and 80:20; and (iii) water.

20. A liquid formulation as claimed in claim 2 containing at least or about 620 ae g/L of glyphosate.

21. A liquid formulation as claimed in claim 1, wherein the amido-amine surfactant is selected from the group R1-amidoalkylamino-R2,R3, where R1 is selected from the group comprising branched or straight C8-C18 alkyl radicals, and R2,R3 are independently chosen from branched or straight C2-C8 alkyl radicals.

22. A liquid formulation as claimed in claim 1, wherein the ester-amine surfactant is selected from the group R1-ester-alkylamino-R2,R3, where R1 is selected from the group comprising branched or straight C8-C18 alkyl radicals, and R2,R3 are independently chosen from branched or straight C2-C8 alkyl radicals.

23. A stable liquid formulation including approximately 625 ae g/L of glyphosate, approximately 62 g/L of a surfactant being the amido reaction product of coco fatty acid and N1,N1-dimethyl-1,3-diaminopropane, approximately 227 g/L of potassium hydroxide, approximately 56 g/L of monoisopropylamine, approximately 14 g/L of phosphoric acid, approximately 378 g/L of water and, optionally, approximately 1.2 g/L of an anti-foaming agent.

24. A method for preparing a stable liquid glyphosate-containing formulation including the steps of:
   (a) forming a wetter package by combining approximately: (i) 37.5 parts by weight of a surfactant being the amido reaction product of coco fatty acid and N1,N1-dimethyl-1,3-diamonipropane; (ii) 9.7 parts by weight of 85% phosphoric acid; and (iii) 52.8 parts by weight of water; and
   (b) then combining the wetter package with glyphosate technical (95% purity), potassium hydroxide (48% in water), monoisopropylamine, anti-foaming agent and water in the weight ratio 166.40:658:227.24:56.40:1.20:290, respectively.

* * * * *